United States Patent [19]

Vince

[11] 4,338,310

[45] Jul. 6, 1982

[54] ALKOXYALKANOATE ESTERS OF ARABINOFURANOSYLADENINE

[75] Inventor: Robert Vince, St. Paul, Minn.

[73] Assignee: The Regents of the University of Minnesota, Minneapolis, Minn.

[21] Appl. No.: 225,567

[22] Filed: Jan. 16, 1981

[51] Int. Cl.$^3$ ........................ A61K 31/70; C07H 19/16
[52] U.S. Cl. ...................................... 424/180; 536/24; 536/26
[58] Field of Search .................... 424/180; 536/24, 26

[56] References Cited

U.S. PATENT DOCUMENTS

| | | | |
|---|---|---|---|
| 3,651,045 | 3/1972 | Haskell et al. | 424/180 |
| 4,048,432 | 9/1977 | Baker | 536/24 |
| 4,055,717 | 10/1977 | Baker et al. | 536/24 |
| 4,055,718 | 10/1977 | Baker | 536/24 |

Primary Examiner—Blondel Hazel
Attorney, Agent, or Firm—Paul H. Ginsburg; Anita W. Magatti; Bruce M. Eisen

[57] ABSTRACT

Alkoxyalkanoate esters of vidarabine of the formula

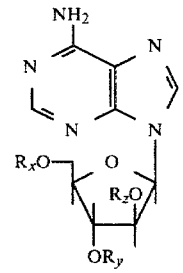

wherein $R_x$, $R_y$ and $R_z$ are

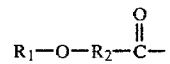

or hydrogen and wherein $R_1$ is lower alkyl and $R_2$ is lower alkylene, which compounds are useful in treating susceptible viral infections, are disclosed.

16 Claims, No Drawings

ALKOXYALKANOATE ESTERS OF ARABINOFURANOSYLADENINE

The present invention relates to alkoxyalkanoate esters of arabinofuranosyladenine. These esters are useful in the treatment of certain viral infections. The present invention also relates to topically or parenterally acceptable formulations of these esters and to the use of these esters in treating susceptible viral infections. The composition of the present invention are particularly effective on the skin.

The nucleoside 9-β-D arabinofuranosyladenine (Ara-A), also known as vidarabine, is presently used as an antiviral agent. Unfortunately, however, it has certain disadvantages. The compositions of the present invention are surprisingly more effective than Ara-A in treating viral infections.

The compounds of the present invention are compounds of the formula

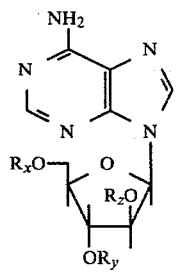

wherein $R_x$, $R_y$ and $R_z$ are

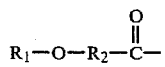

or hydrogen and at least one of $R_x$, $R_y$ and $R_z$ is

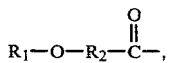

wherein $R_1$ is a lower alkyl radical having 1 to 6 carbons and $R_2$ is an alkylene radical having 1 to 6 carbons. An example of a monoester is a compound of the formula I wherein $R_x$ is

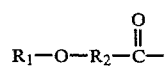

and $R_y$ and $R_z$ are hydrogen. An example of a diester is a compound of the formula I wherein $R_x$ and $R_y$ are

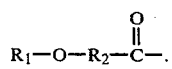

Of the compounds of the present invention, the monoesters are preferred. In a particularly preferred embodiment, $R_x$ is methoxyacetyl and $R_y$ and $R_z$ are hydrogen.

The compounds of the present invention are prepared by reaction of 9-β-D-arabinofuranosyladenine with from one to three equivalents of an alkoxyacid halide of the formula

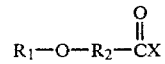

wherein $R_1$ is a lower alkyl group having from 1 to 6 carbons $R_2$ is an alkylene radical having 1 to 6 carbons, and X is halogen. Preferably $R_1$ is $CH_3$ and $R_2$ is $-CH_2-$. The alkoxyacid halide is added to a solution of arabinofuranosyladenine in a non-polar, nonreactive, water-miscible solvent, such as dimethylformamide, dimethylacetamide, tetrahydrofuran, pyridine, or the like. The reaction is carried out at about 4° C. for about 18-24 hours with stirring. Water or aqueous sodium bicarbonate is added to quench the reaction. Volatiles are removed and the ester product is recovered and purified. The monoester results from the reaction of one equivalent of the alkoxyacid halide, the diester from two equivalents, and the triester from three equivalents.

After preparation of a monoester or a diester, it is possible to use a different alkoxyhalide of the formula

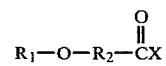

in order to prepare a diester or triester. In this manner, esters having two or three different

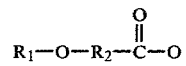

groups may be prepared. While such esters are included within the scope of the present invention, esters having only a single type of

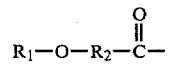

group are more conveniently prepared and are, thus, preferred.

The following Examples illustrate the preparation of the compounds of the present invention:

EXAMPLE 1

9-β-D-Arabinofuranosyladenine-5'-methoxyacetate (where

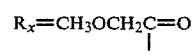

$R_y = R_z = H$). Arabinofuranosyladenine (4.8 g, 18 mmoles) was dissolved in dry dimethylformamide (150 ml) by warming and the solution was cooled to 0° C. Methoxyacetyl chloride (2.38 g, 22 mmoles) in dimethylformamide (20 ml) was added dropwise with stirring and the reaction mixture was stirred overnight at 4° C.* Ice water (20 ml) containing sodium bicarbonate (2.38 g) was added to neutralize the solution. The solvents were removed under reduced pressure and the residue was stirred in 15% methanol/chloroform. The inorganic solid was removed by filtration and the filtrate was applied to a silica gel column and eluted with 15% methanolic chloroform. The major product fraction was evaporated and the residue was dissolved in water and refrigerated overnight. The white solid product was removed by filtration and gave 3.9 g (yield 59%) of the title compound: m.p. 74° C.

*If thin-layer chromatrograph indicates significant amount of remaining Ara-A, methoxyacetyl chloride (1 g) in dimethylformamide is added and the mixture is allowed to stir for an additional 18 hours at 4° C.

Anal. Calculated for $C_{13}H_{17}N_5O_6 \cdot \frac{1}{2}H_2O$: C, 44.82; H, 20.10; N, 5.21. Found: C, 44.66; H, 19.96; N, 5.18.

EXAMPLE 2

9-$\beta$-D-Arabinofuranosyladenine-3',5'-di-methoxyacetate where $$R_x = R_y = CH_3OCH_2C=O;$$

and $R_z = H$). The diester was prepared by the same procedure as described in Example 1, using 18 mmoles of arabinofuranosyladenine and 40 mmoles of methoxyacetyl chloride, and allowing the reaction mixture to stir at 4° C. overnight and then at 25° C. for an additional 24 hours.

The major fraction was obtained from a silica gel column using the same workup procedure described in example 1.

EXAMPLE 3

9-$\beta$-D-Arabinofuranosyladenine-2',3',5'-tri-methoxyacetate (where $R_x = R_y = R_z = CH_3OCH_2C=O$). The triester was prepared by the same procedure as described in example 1, using 18 mmoles of arabinofuranosyladenine and 50 mmoles of methoxyacetyl chloride. The reaction mixture was stirred at 4° C. overnight and then at 25° C. for an additional 24 hours. The major fraction was obtained from a silica gel column using the same workup procedure described in example 1.

Similarly prepare 9-$\beta$-D-arabinofuranosyladenine-5'-(7-hexyloxyheptanoate); 9-$\beta$-D-arabinofuranosyladenine-5'-(4-propyloxybutyrate); 9-$\beta$-D-arabinofuranosyladenine-5'-(4-ethoxybutyrate); and 9-$\beta$-D-arabinofuranosyladenine-3',5'-di-O-(5-ethoxyvalerate).

The compounds of the present invention may be used in the treatment of infections, particularly those of mammals (e.g. humans), caused by DNA-containing viruses such as Herpes viruses, including types I and II and Herpes zoster. They can also be used in the treatment of adenoviruses, papovaviruses (which cause warts), picodnaviruses and poxviruses.

The subject alkoxyalkanoate esters can be formulated in standard fashion with conventional pharmaceutical excipients for topical dosage forms. Such formulations should contain about 5 to 20% by weight, preferably about 10 to 15% by weight, of these esters. For application to the skin, the concentration is desirably in the range of about 5 to 20% by weight, preferably about 10 to 15% by weight, and most preferably about 15% by weight. Standard dermatological cream and ointment bases can be employed in the usual manner. For treatment of susceptible viral infections of the eyes or genital areas, standard ophthalmic and vaginal bases, respectively, such as creams or solutions can be employed.

In a typical regimen, topically acceptable formulations of this invention are applied four times daily to the affected site for a period of five to fourteen days until the infection clears. These compositions can be applied to the infected site in the usual manner. Semi-solid dosage forms can be spread manually or with an applicator, and liquid forms can be applied by dropper or spray.

The compounds of the present invention may also be administered parenterally, in parenterally acceptable vehicles, in the treatment of herpes virus encephalitis, shingles, disseminated varicella, cytomegalovirus infection, and the like.

The following one-gram formulations are exemplary of the products of the invention.

EXAMPLE 4

| Topical Cream | |
|---|---|
| 9-$\beta$-D-Arabinofuranosyladenine-5'-methoxyacetate | 150 mg |
| propylene glycol | 100 mg |
| 4-chloro-m-cresol | 1 mg |
| sodium phosphate, monobasic monohydrate | 2.7 mg |
| phosphoric acid | 0.02 mg |
| white petrolatum | 150 mg |
| polyethylene glycol monocetyl ether | 18 mg |
| cetostearyl alcohol | 72 mg |
| mineral oil | 60 mg |
| q.s. water, purified U.S.P. | |

EXAMPLE 5

| Topical Ointment | |
|---|---|
| 9-$\beta$-D-Arabinofuranosyladenine-5'-methoxyacetate | 150 mg |
| mineral oil | 50 mg |
| q.s. white petrolatum | |

EXAMPLE 6

| Ophthalmic Ointment | |
|---|---|
| 9-$\beta$-D-Arabinofuranosyladenine-5-'-methoxyacetate | 150 mg |
| methyl paraben | 0.5 mg |
| propyl paraben | 0.1 mg |
| q.s. white petrolatum | |

It is apparent that many modifications and variations of this invention as hereinbefore set forth may be made without departing from the spirit and scope thereof. The specific embodiments described are given by way of example only and the invention is limited only by the terms of the appended claims.

I claim:

1. A compound of the formula:

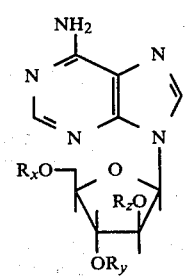

wherein $R_x$, $R_y$ and $R_z$ are

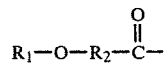

or hydrogen and at least one of $R_x$, $R_y$ and $R_z$ is

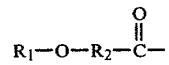

and $R_1$ is a lower alkyl radical having 1 to 6 carbons and $R_2$ is an alkylene radical having from 1 to 6 carbons.

2. A compound according to claim 1, wherein $R_x$ is

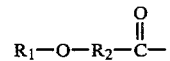

and $R_y$ and $R_z$ are hydrogen.

3. A compound according to claim 1, wherein $R_x$ and $R_y$ are

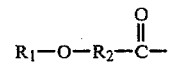

and $R_z$ is hydrogen.

4. A compound according to claim 1, wherein $R_x$, $R_y$ and $R_z$ are

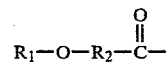

5. A compound according to claim 1, wherein $R_1$ is $CH_3$ and $R_2$ is $-CH_2-$.

6. A compound according to claim 5, wherein $R_x$ is

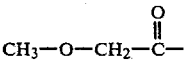

and $R_y$ and $R_z$ are hydrogen.

7. A compound according to claim 5, wherein $R_x$ and $R_y$ are

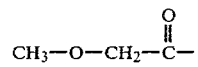

and $R_z$ is hydrogen.

8. A compound according to claim 5, wherein $R_x$, $R_y$ and $R_z$ are

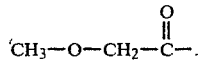

9. A topical antiviral composition for treating susceptible viral infection comprising an antivirally effective amount of a compound of claim 1 in a topically acceptable vehicle.

10. A topical antiviral composition for treating susceptible viral infection comprising an antivirally effective amount of a compound of claim 6 in a topically acceptable vehicle.

11. A method of treating susceptible viral infections comprising applying to the infected area of a mammal a composition of claim 9.

12. A method of treating susceptible viral infections comprising applying to the infected area of a mammal a composition of claim 10.

13. A parenteral antiviral composition for treating susceptible viral infection comprising an antivirally effective amount of a compound of claim 1 in a parenterally acceptable vehicle.

14. A parenteral antiviral composition for treating susceptible viral infection comprising an antivirally effective amount of a compound of claim 6 in a parenterally acceptable vehicle.

15. A method of treating susceptible viral infections comprising administering to the infected mammal a composition of claim 13.

16. A method of treating susceptible viral infections comprising administering to the infected mammal a composition of claim 14.

* * * * *